United States Patent
Keith et al.

(10) Patent No.: US 9,480,794 B2
(45) Date of Patent: Nov. 1, 2016

(54) SYSTEM AND METHOD FOR DETECTING OCCLUSIONS IN A MEDICATION INFUSION SYSTEM USING PULSEWISE PRESSURE SIGNALS

(71) Applicant: Becton, Dickinson and Company, Franklin Lakes, NJ (US)

(72) Inventors: Steven Keith, Madison, WI (US); Elaine McVey, Durham, NC (US); Frances Tong, Chapel Hill, NC (US); Ronald J. Pettis, Cary, NC (US); Joshua Herr, Fair Lawn, NJ (US); Richard J. Klug, Roxboro, NC (US); Christopher Rini, Raleigh, NC (US); Natasha Bolick, Raleigh, NC (US); Alfred Joseph Harvey, Raleigh, NC (US); Vincent J. Sullivan, Cary, NC (US); Matthew S. Ferriter, Chapel Hill, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/050,207

(22) Filed: Oct. 9, 2013

(65) Prior Publication Data
US 2014/0107613 A1   Apr. 17, 2014

Related U.S. Application Data

(60) Provisional application No. 61/713,096, filed on Oct. 12, 2012.

(51) Int. Cl.
*A61M 31/00* (2006.01)
*A61M 5/168* (2006.01)
*A61M 5/142* (2006.01)
*A61M 5/50* (2006.01)

(52) U.S. Cl.
CPC .......... *A61M 5/16854* (2013.01); *A61M 5/142* (2013.01); *A61M 5/5086* (2013.01); *A61M 2005/16863* (2013.01); *A61M 2205/18* (2013.01); *A61M 2205/3355* (2013.01)

(58) Field of Classification Search
CPC .......... A61M 5/142; A61M 5/16854; A61M 5/5086; A61M 2005/16863; A61M 2205/18; A61M 2205/3355; A61M 5/16831; A61M 5/16859; A61M 2005/16868; A61M 2205/3331; A61M 2005/16872; Y10S 128/12
USPC ........................................ 604/506
See application file for complete search history.

(56) References Cited

U.S. PATENT DOCUMENTS 4,534,756 A * 8/1985 Nelson ................. A61M 5/365
                                                      604/505
5,096,385 A    3/1992 Georgi et al.

(Continued)

FOREIGN PATENT DOCUMENTS

WO    WO2010046728 A1    4/2010

*Primary Examiner* — Jason Flick
(74) *Attorney, Agent, or Firm* — Dickinson Wright PLLC

(57) ABSTRACT

A medical fluid communication system is disclosed comprising a pump controller and a fluid detector. The fluid detector detects characteristics of the fluid and provides fluid measurements to the pump controller, which detects if the fluid is flowing in the medication delivery system. In the event fluid is not flowing due to an occlusion, the pump controller may attempt to resolve the occlusion or may provide a warning to a user that an occlusion is occurring.

8 Claims, 9 Drawing Sheets

(56) References Cited

U.S. PATENT DOCUMENTS

| | | |
|---|---|---|
| 5,800,387 A | 9/1998 | Duffy et al. |
| 6,656,148 B2 | 12/2003 | Das et al. |
| 7,621,893 B2 | 11/2009 | Moberg et al. |
| 7,726,328 B2 | 6/2010 | Christensen et al. |
| 7,828,528 B2 | 11/2010 | Estes et al. |
| 7,938,797 B2 | 5/2011 | Estes |
| 8,007,460 B2 * | 8/2011 | Gelfand ................. A61B 5/201 604/31 |
| 8,081,069 B2 | 12/2011 | Haueter et al. |
| 8,267,893 B2 | 9/2012 | Moberg et al. |
| 8,568,349 B2 | 10/2013 | Shergold |
| 2004/0127844 A1 * | 7/2004 | Flaherty ............ A61M 5/14248 604/67 |
| 2010/0168607 A1 | 7/2010 | Miesel |

\* cited by examiner

SYSTEM AND METHOD FOR DETECTING OCCLUSIONS IN A MEDICATION INFUSION SYSTEM USING PULSEWISE PRESSURE SIGNALS

This application claims the benefit under 35 U.S.C. §119 (e) of U.S. provisional application No. 61/713,096, filed Oct. 12, 2012, the entire contents of which are hereby incorporated by reference.

BACKGROUND OF THE INVENTION

1. Field of the Invention

The present invention relates to infusion of medication into patient and, more particularly, to a system and method for detecting occlusion in a medication infusion system using pulsewise pressure signals.

2. Description of the Related Art

Occlusion of a fluid path is a complication where either the delivery to or withdrawal of fluid from a patient is partially or completely restricted. These include devices for SC, IM, ID and intravenous (IV) delivery, access and sampling. For example, in an ambulatory insulin infusion system, both basal rate and bolus delivery of a medication fluid to a patient is typically provided by delivery of microboluses or fluid pulses through a fluid path (e.g., a tube) to generate the composite target total delivery volume and rate, and delivered to the patient via an infusion set. Generally, the boluses during the basal infusion are periodically delivered in short pulses over a regular interval (such as a period of 3 minutes) via a servo motor that actuates a piston. The actuated piston moves and biases the fluid in a fluid reservoir, thereby decreasing volume in the fluid reservoir and causing a controlled amount of medication fluid to flow from the fluid reservoir and into the fluid path. The infusion set receives the fluid flow and communicates the fluid into the patient. After delivering the bolus, the system waits for the period to expire to initiate a next delivery of medication. During delivery of higher volumes (such as for post-prandial meal boluses), the size of the small individual pulses may be increased and/or the time interval decreased to provide a greater total fluid volume and increased delivery rate.

As the fluid flows through the tube toward the infusion set, the induced pressure in the infusion system decays as a result of losses due to mechanical forces (e.g., static and dynamic friction, and so on). Further, other external or internal factors may further impede the flow of fluid. A partial kink in the tubing would reduce cross-sectional area in the fluid path, thereby reducing the rate of fluid able to traverse the fluid path and increasing pressure in the fluid path. The fluid path may be impeded by other factors such as crystal formation in the fluid, the presence of gaseous bubbles, impurities or other particles, backpressure from tissues in the patient, physical movement of the patient, movement of the fluid path, non-compliance of elastomeric components in the fluid path, and so on. When the fluid path is disrupted by any internal or external reason, the fluid path may experience a complete or partial occlusion that affects delivery of the medication fluid to the patient.

The flow of the medication fluid in the fluid path is currently detected by measuring the force applied to the piston during piston actuation as described above. However, the force applied to the piston can reflect static and dynamic friction forces associated with the piston mechanism in addition to pressure in the fluid path. Thus, the force applied to the piston represents the combined static friction, dynamic friction, other mechanical forces in addition to fluid pressure. The fluid pressure may in fact be a relatively small component of the overall force applied to reservoir piston, and accordingly piston force is not necessarily directly correlated to the pressure in the fluid path at the location of medication delivery. As a result, sensitivity is limited in these types of systems since the static and dynamic friction forces within the fluid reservoir dominate below approximately 2 psi. It may take multiple piston movements to determine that there is an occlusion occurring in the fluid path that is presently affecting medication delivery. Further, in the event that the pressure of the fluid reservoir is low, the static and dynamic friction forces associated with piston movement may be larger than the force required to move the liquid, thereby causing the pressure measurements during piston movement to be inaccurate and prevent detection of occlusions.

Occlusion events are responsible for premature removal of 5-15% of vascular access devices such as peripheral intra venous catheters (PIVCs) that are used both for patient fluid sampling and medication delivery. Evidence suggests that timed or scheduled removal of PIVC catheters without cause may not benefit patients and may add cost to healthcare treatment. In a PIVC catheter, occlusion may be a result of mechanical phenomena such as kinking or impingement of the catheter tip against the intima, biochemical effects such as precipitation of the infusate, and thrombus formation. In particular, thrombus aggregation in a catheter may cause an occlusion event that leads to other complications such as phlebitis. In a PIVC catheter, blood can enter the catheter during events such as placement of the catheter, as a result of pressure changes from movements of the catheter or associated tubing, during checks performed by medical staff, as a result of improper or incomplete flushing of the catheter, or via blood sampling. Each blood exposure event in the catheter can lead to build up of thrombus within or around a catheter to form a clot that reduces the diameter of the flow path. Consequently, more pressure is needed to deliver the same amount of fluid at a given rate with potentially dangerous consequences for the patient.

In conventional systems an occlusion in the fluid path may be detected too slowly or not at all in some circumstances, with potentially dangerous consequences for the patient. For instance, if an undetected occlusion occurs during insulin infusion, the patient may not receive a necessary amount of medication to prevent a potentially dangerous hyperglycemic event. Because the delivery of the medication fluid may be vital in delivery of medical service, there is a need for rapid detection of occlusions in medication delivery systems.

SUMMARY OF THE INVENTION

Disclosed is a system and method for detecting occlusions in a medication fluid communication system or venous access device comprising a fluid reservoir, a fluid path connected between the fluid reservoir and a patient, a fluid delivery mechanism, and a pressure sensor measuring a pressure of the fluid within the fluid path. The method includes measuring pressure of a medication fluid in a fluid path of a medication delivery system during a current interval. Based on the pressure measurements, the method determines if a flow of the medication fluid is successful, reduced, or unsuccessful.

Also disclosed is another system and method for detecting occlusions in a medical fluid communication system having a fluid reservoir, a fluid path connected between the fluid reservoir and a patient, a fluid delivery device, and a pressure sensor measuring a pressure of the fluid within the fluid path. The method measures a pressure of a medication fluid in a fluid path of a medication fluid communication system during a current interval and compares the minimum pressure of the current interval to a predetermined threshold pressure. The predetermined threshold is based on a calculation of a peak pressure of the previous interval and a minimum pressure of the previous interval. The method determines if a flow of the fluid is not successful if the minimum pressure exceeds the predetermined threshold and determining if the flow of the medical fluid is successful if the minimum pressure does not exceed the predetermined threshold.

BRIEF DESCRIPTION OF THE DRAWING FIGURES

These and other features and advantages of the present invention will become more apparent from the detailed description of exemplary embodiments with reference to the attached drawings in which.

Throughout the drawings, like reference numerals will be understood to refer to like features and structures.

DETAILED DESCRIPTION OF EXEMPLARY EMBODIMENTS

Reference is now made in detail to exemplary embodiments of the invention, which, together with the drawings and the following examples, serve to explain the principles of the invention. Those of ordinary skill in the art will appreciate that the embodiments described herein are merely exemplary, and are described in detail to enable those skilled in the art to practice the invention, and it is to be understood that other embodiments may be utilized, and various changes to the embodiments described herein may made without departing from the spirit and scope of the present invention. Unless otherwise defined, all technical and scientific terms used herein have the same meaning as commonly understood by those of ordinary skill in the art to which this invention belongs. Although any methods and materials similar or equivalent to those described herein can be used in the practice or testing of the present invention, the example methods, devices and materials are now described.

Figure 1:
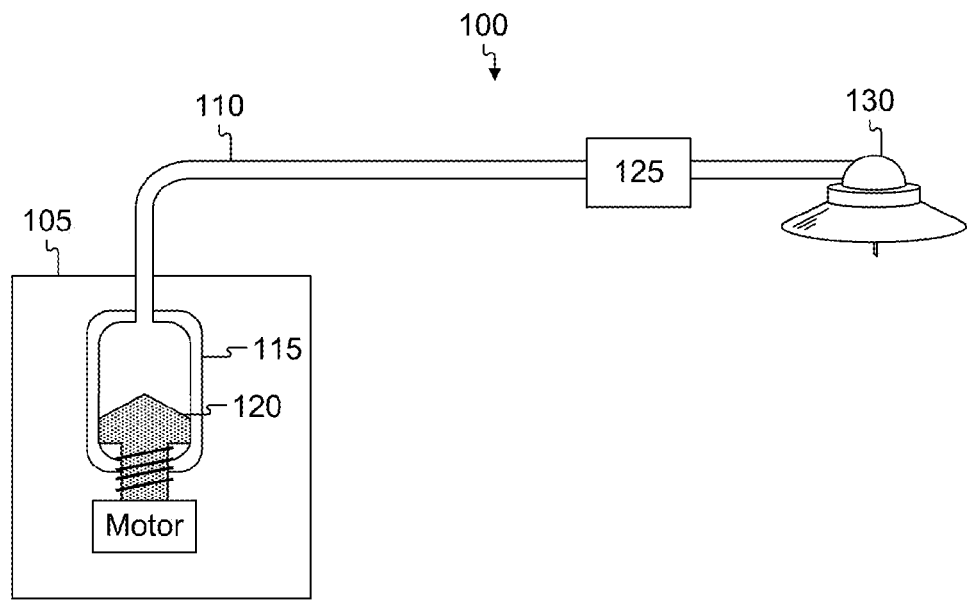
FIG. 1 illustrates and example medication delivery system in accordance with an exemplary embodiment of the present invention.

FIG. 1 illustrates an example medication delivery system 100 that detects partial or complete occlusions during delivery of medication fluid to a patient or sampling or withdrawal of fluid from a patient. The medication delivery system 100 generally operates by delivering minute boluses (such as 0.5 microliters) to a patient over a short pulse (such as 100 milliseconds, 1 second, and so on) at regular intervals (such as a period of 3 minutes, or the like). The medication delivery system 100 includes a pump controller 105 that delivers a pulse of medication fluid to a patient via a fluid path such as tubing 110. In the example of FIG. 1, the pump controller 105 includes a fluid reservoir 115 containing the medication fluid. In this example, the fluid reservoir 115 is configured to interface with a piston 120 that is mechanically displaced within the fluid reservoir 115 by any suitable mechanism, such as a servo motor. In other examples, any device suitable for delivering controlled dosages of fluid could perform the medication fluid delivery. By actuating the piston 120, the piston 120 is axially displaced within the fluid reservoir 115, and thereby reduces the available volume within the fluid reservoir 115. As such, the pressure within the fluid reservoir 115 increases and causes a controlled volume of the medication fluid to flow into the tubing 110 toward the patient. That is, a pressure pulse, which causes the medication fluid to flow, travels from the fluid reservoir 115 through the tubing 110 at a velocity that depends on the characteristics of the fluid path, the medication fluid, and so forth.

The medication delivery system 100 includes a fluid detector 125 that receives and measures characteristics of the pressure pulse in the medication fluid to determine if it is flowing in the medication delivery system 100 and being delivered to the patient. In the example of FIG. 1, the fluid detector 125 is placed inline with tubing 110 and in proximity with an infusion set hub 130 containing an infusion cannula that delivers the medication fluid into the patient. That is, the fluid detector 125 is in fluid communication with the tubing 110, the fluid reservoir 115, and the infusion set hub 130. Preferably, the fluid detector 125 is placed in proximity to the infusion set hub 130 to measure the pressure of the medication fluid close to the location of medication delivery to the patient. In other examples, the fluid detector 125 may be integrated within the infusion set hub 130. Alternatively, the fluid detector 125 may be disposed adjacent to or integrated within the fluid reservoir 115. In another example, multiple fluid detectors 125 may be implemented at several positions along the fluid path to detect pressure at different locations of the fluid path.

The fluid detector 125 receives the medication fluid and measures any suitable characteristic of the fluid such as pressure, temperature, force, flow rate, volume, conductance, resistance and so forth. The fluid detector 125 then communicates the measurement results to the pump controller 105, which uses the fluid measurements to determine if the medication fluid is sufficiently flowing in the fluid path and being delivered to the patient. In one example, the fluid detector 125 may transmit the fluid measurements to the pump controller 105 via a wireless interface. In other examples, the fluid detector 125 may transmit the measurements via a wired interface, such as an electrical conductor embedded in the tubing 110, or the like.

Figure 2:
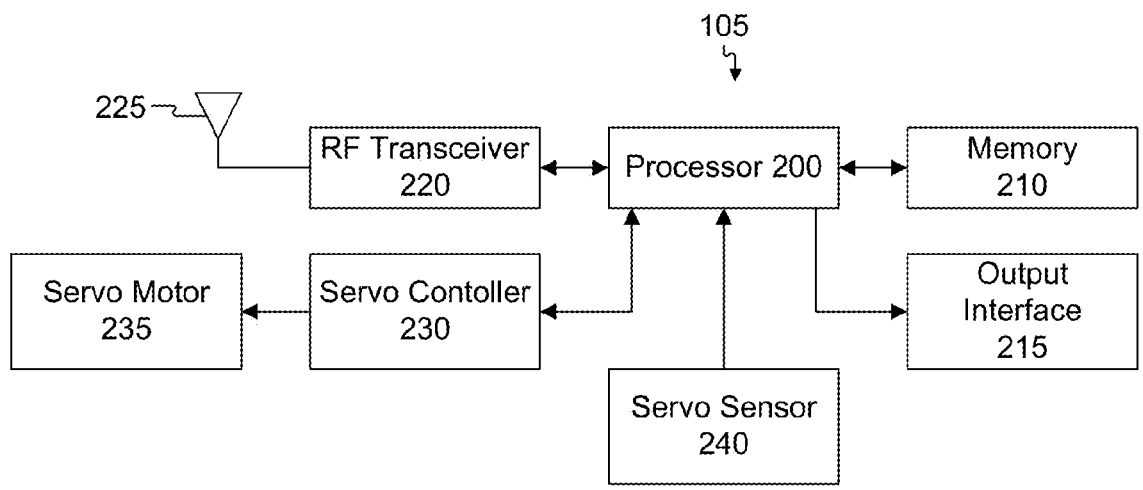
FIG. 2 depicts a block diagram of an example pump controller of the medication delivery system of FIG. 1.

FIG. 2 illustrates a block diagram of an example pump controller 105 that controls the operation of the medication delivery system 100 by receiving the measurements from the fluid detector 125 shown in FIG. 1. In the example of FIG. 2, a processor 200 receives the fluid measurements via any suitable interface, such as an analog-to-digital converter, a modulated input, or the like. The fluid measurements are stored in a memory 210 which can be separate or integral with the processor 205. Using the fluid measurements, the processor 205 determines if an occlusion has occurred and generates an output via output interface 215 to provide notice of the occlusion. The output interface 215 is generally any output mechanism that displays a warning to a health care professional or patient to provide notice of an occlusion. For instance, the pump controller 105 may include a liquid crystal display (LCD) that outputs pressure measurements to the health care professional and, in the event an occlusion is determined to be occurring, can output a display indicator on the LCD to provide such notice. In other examples, a light emitting diode (LED) may be activated or modulated, an audible event such as an alarm may be output, or a haptic event such as a vibration via a vibration motor (not shown) via the output interface 215.

The example pump controller 105 of FIG. 2 includes a RF transceiver 220 for sending and receiving data to and from the fluid detector 125 via an antenna 225. In such an example, the RF transceiver 220 may be implemented by a custom application specific integrated circuit (ASIC) or may be implemented by over-the-shelf solutions, such as Zigbee®, Bluetooth®, or any other suitable method.

The pump controller also includes a servo controller 230 for actuating a servo motor 235 for driving the piston 120 to cause fluid to flow from the fluid reservoir 115. In other examples, the servo controller 230 may be integral with processor 200. Further, the pump controller 105 may also include a servo sensor 240 to detect pressure applied to the piston during piston 120 movement during medication delivery.

Figure 3:
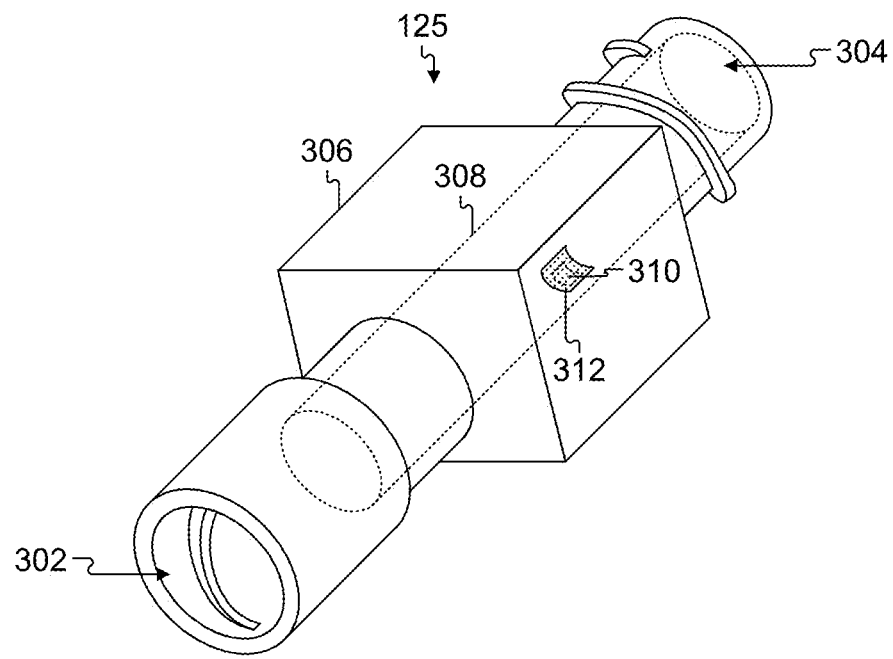
FIG. 3 is a perspective view of an example fluid detector of the medication delivery system of FIG. 1.

FIG. 3 is a perspective view of an exemplary in-line fluid detector 125 that is potentially implemented via a standard inline medical connector such as a Luer-Lok®, Safety-Lok®, or any other suitable connector. That is, the fluid detector 125 includes a female connector 302 disposed at a proximal end and a male connector 304 disposed at a distal end to allow the fluid detector 125 to be connected inline between the tubing 110 and the infusion set 130. The fluid detector 125 includes a mechanical housing 306 disposed between the female connector 302 and male connector 302 and includes a fluid path 308 to permit fluid flow and to detect a property of the flowing fluid, such as the pressure of the fluid.

The fluid path 308 includes a sensor 310 that detects a suitable characteristic of the fluid such as pressure. In other examples, the pressure may be measured in conjunction with other characteristics to improve fluid detection, such as temperature, viscosity, or any other suitable characteristic. In the example of FIG. 3, the sensor 310 is substantially encapsulated by a shield 312, preferably constructed of a polymer, or the like, to physically isolate the sensor 310 from the fluid path and prevent any contact with the medication fluid. However, in other examples, the sensor 310 may directly contact the medication fluid. In the example of FIG. 3, the sensor 310 is a strain gauge that detects pressure of the medication fluid in the fluid path 308. Thus, to provide the most accurate pressure measurements, the fluid detector 125 is preferably placed close to the infusion set to provide the most accurate pressure measurement of the medication fluid flow. In other examples, the sensor 310 may be implemented by any suitable mechanism to detect the suitable characteristic of the fluid, such as an electromagnetic pressure sensor, a piezoelectric sensor, an optical sensor, a potentiometric sensor, a thermal sensor, or any other suitable characteristic sensor.

In other examples, the fluid detector 125 may be integrated within the infusion set hub, thereby detecting flow of the medication fluid at the location of delivery to a patient. In another example, the fluid detector 125 may include a standard or proprietary connector adapted to receive both medication fluid and electrical signals in a single integral connector. In such an example, the fluid detector 125 may be adapted to send the measurement data as electrical data via tubing 110 having electrically conductive members therein that are isolated from the fluid path. Further, such electrical signals provided via the conductive members may be configured such that medication fluids are not affected by the data transmission. In other words, the medication fluid is preferably isolated from electromagnetic fields, and the like.

Figure 4:
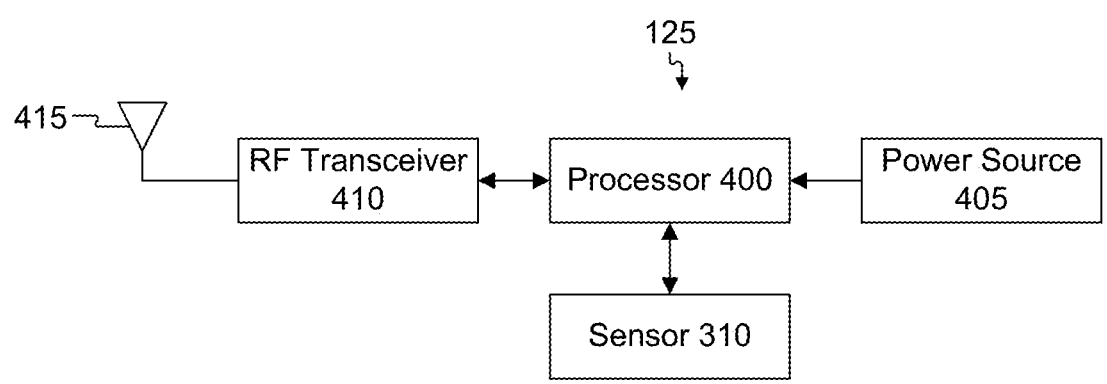
FIG. 4 depicts a block diagram of an example fluid detector of the medication delivery system of FIG. 1.

FIG. 4 illustrates an example block diagram of a fluid detector 125 disposed in the mechanical housing 306 and detects characteristics of the fluid in fluid path 308 as described in detail above. The fluid detector 125 includes a processor 400 that is implemented by any suitable device for detecting the measurements of the sensor 310 and providing the results to the pump controller 105, such as a logic circuit, an ASIC, an FPGA, a microcontroller, a microprocessor, or the like. That is, the sensor 310 is coupled to an input on the processor 400. Generally, a highly integrated processing device such as a microcontroller having an integrated analog-to-digital converter and memory is preferred due to advantageous size and power characteristics. The processor 400 is configured to receive power from an power source 405 of the fluid detector 125 that may be integral or extrinsic. In other examples, the integral power source 405 may be provided via inductive coupling to an inductor that receives wireless signals and converts the magnetic field into electric power.

The fluid detector 125 also preferably includes a RF transceiver 410 that sends and receives data via antenna 415. In one example, the fluid detector 125 may receive an instruction to measure the fluid pressure via a wireless transmission from the pump controller 105. In response, the processor 400 may induce the sensor 310 to provide a measurement on at least one input. For example, in the event the sensor 310 is implemented via a strain gauge in the fluid path 308, a first voltage is applied to the sensor 400 via an output of processor 400. An input of processor 400 receives second voltage that is reduced via the electrical resistance of the strain gauge and calculates the strain pressure applied to the sensor 310. Further, the processor 400 may calculate a normalized pressure based on a nominal strain pressure to determine the pressure of the fluid in the fluid path 308. Of course, the sensor 310 need not receive specific commands for measuring a fluid characteristic, and may instead simply make measurements at predetermined intervals, and provide measurements to the processor 400.

By having an in-line sensor 310, the sensitivity of fluid characteristic measurement is increased. As will be appreciated, an in-line pressure sensor directly measures fluid pressure, as opposed to a force measurement device coupled to a piston 120 within a reservoir 115, eliminating the sometimes dominating force components contributed by static and dynamic friction, and the like, associated with the piston.

Figure 5:
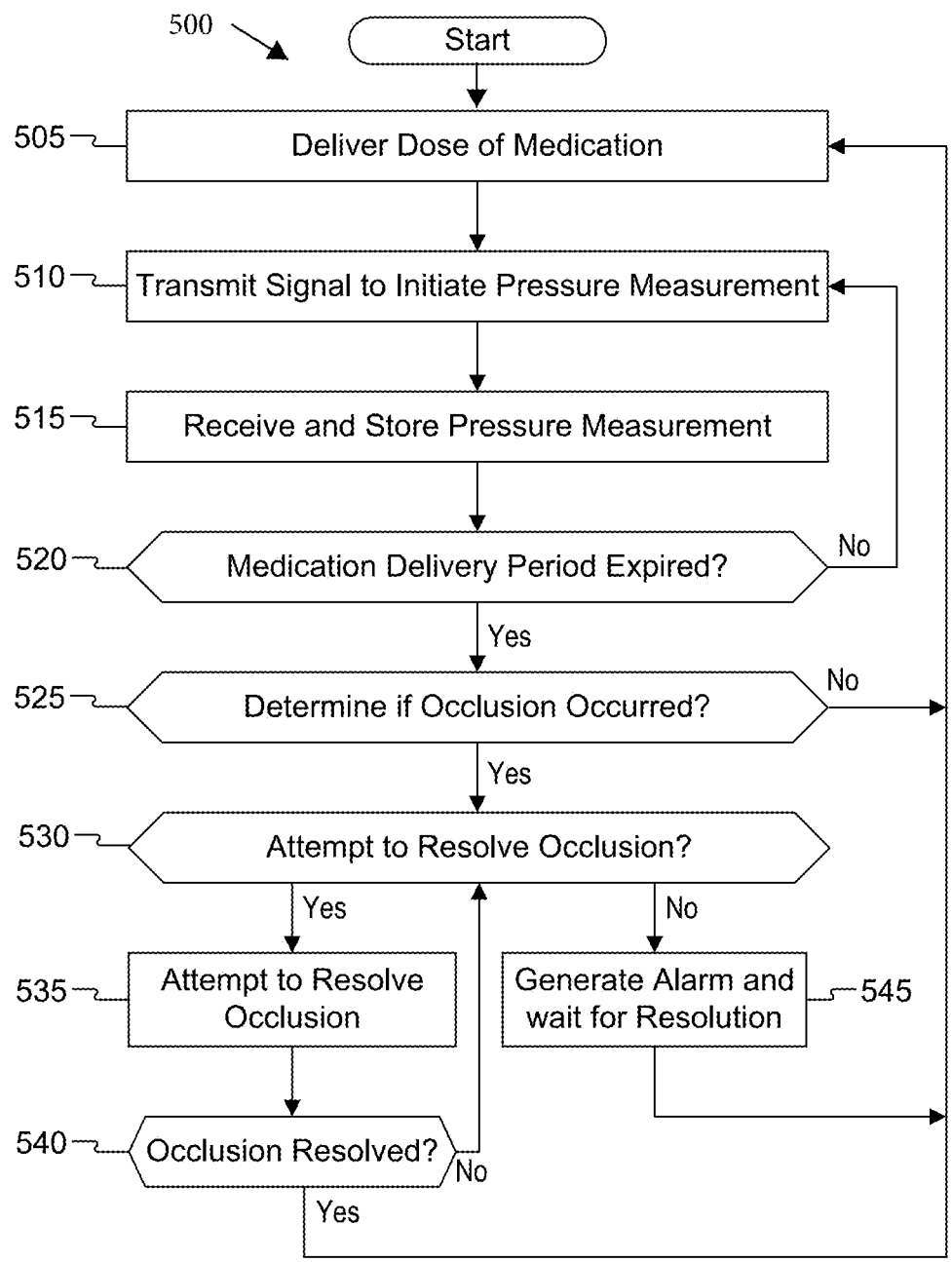
FIG. 5 illustrates a flowchart of an example process that the medication delivery system may implement in accordance with an exemplary embodiment of the present invention.

FIG. 5 illustrates an example process 500 for detecting occlusion in the medication delivery system during treatment of a patient. Generally, a medication delivery interval begins with a delivery of a dose of the medication fluid and continues until the next medication delivery occurs. Initially, at step 505, the example process 500 and the medication delivery interval begin by delivering a dose of medication fluid at step 505. In one example, the pump controller then transmits a signal to initiate a pressure measurement in the fluid path at step 510. In response, the fluid detector measures the fluid pressure in the fluid path and transmits the pressure measurement to the pump controller, which stores the pressure measurement at step 515. After receiving the pressure measurement, the example process 500 determines if the current medication delivery interval has expired at step 520. If the current medication delivery interval has not expired at step 520, the example process 500 returns to step 510 to transmit a signal to initiate and receive the next pressure measurement in the current medication delivery interval.

If the current medication delivery interval has expired at step 520, using the pressure measurements, the example process 500 determines if an occlusion occurred during the current medication delivery interval occurred at step 525. If an occlusion did not occur at step 525, the example process 500 returns to step 505 to initiate a next medication delivery interval that begins with delivering a next dose of the medication fluid.

If an occlusion is determined to have occurred at step 525, the example process 500 may determine if there should be an attempt to resolve the occlusion based on any suitable criteria at step 530. For example, if the maximum pressure exceeds a predefined pressure during a single medication delivery interval, the example process 500 may determine it should attempt to resolve the occlusion at step 535. For example, the example process 500 may generate a very large transient pressure peak by actuating the piston and increasing the rate at which the piston moves. Alternatively, an increased amount of medication fluid is delivered to the patient and the pressures of the medication fluid are measured at various times and then compared after a period of time. In another example of step 535, a drug-free fluid connected to the fluid path as close as possible to the infusion set, which may be delivered such that the drug-free fluid passes through the infusion set and through the delivery location of the patient. Such an example allows the smallest possible amount of medication fluid to be delivered to the patient. In such an example, this medication clearing event could be accompanied by or preceded by a small movement of the piston in the negative direction, that is, increasing the volume in the fluid reservoir such that pressure is normalized, thereby preventing over-medicating the patient. In another example, the infusion set may be manipulated by a high frequency displacement of the infusion set tip by, for example, motion of a piezoelectric device located in the infusion set body or by manual manipulation by the patient or medical professional.

After attempting to resolve the occlusion at step 535, the example process continues at step 540 to determine if the occlusion is resolved. In the event the occlusion is resolved at step 540, the example process 500 returns to step 505 to deliver the next suitable dose of medication in the next appropriate medication delivery interval. For example, process 500 may wait a period of time after resolving the occlusion. On the other hand, if the occlusion is not resolved at step 540, the example process 500 returns to step 530 to determine if it should attempt to resolve the occlusion.

In the event that the example process 500 determines to not attempt resolution of the occlusion at step 530, the example process 500 generates an alarm and waits for resolution of the occlusion at step 545. For example, a message may be output to request the patient to physically manipulate the infusion set to clear an occlusion due to a partial kink and then provide an input to signal that the occlusion event is resolved. In such an example, after the occlusion is resolved by any suitable corrective action, the example process 500 returns to step 505 to deliver the next suitable dose of medication in the next suitable medication delivery interval.

That is, the example process 500 at steps 530-545 waits until the occlusion is resolved before continuing medication delivery. In some examples, after returning to step 505, the example process 500 would continue to compare the pressure measurements with previous pressure measurements prior to the occlusion event to ensure correct delivery of medication. However, in other examples, the example process 500 may flush the previous pressure measurements based on a change in the system that does not substantially affect delivery of the medication, such as a partial occlusion due to the configuration of the fluid path, such as tangling in clothing, for example.

One example implementation of the example process 500 may be a drug delivery feedback system implementing an artificial pancreas. In such an example, knowledge of insulin delivery status will improve delivery of insulin to the patient using real-time insulin delivery data based on the pressure measurements at the fluid detector. Even without knowledge of the concentration of the dosage, the example process 500 uses previous insulin delivery volumes to calculate the preferred delivery volume of medication for the patient at any time. Thus, data regarding incomplete or missing delivery of the insulin would improve performance of such an example system.

Generally, at least two pressure measurements must be measured in each medication delivery interval. In such an example, the example process 500 attempts to measure the actual peak pressure that occurs at the beginning of the medication delivery interval and a minimum pressure that occurs in the latter portion of the medication delivery interval. In other examples, the pressure measurements may be aperiodic to allow the example process 500 to measure at different intervals in the medication delivery interval to allow for rapid detection of occlusions.

Further, although the described example process 500 detects occlusions after the medication delivery interval expires, the example process 500 may be adapted to detect occlusions during medication delivery intervals. For instance, if the peak pressure or the minimum pressure of the fluid exceeds a predefined threshold, the example process 500 may determine that an occlusion has occurred in the current medication delivery interval. Further, if a subsequent peak pressure is greater than a previous peak pressure by a predefined threshold, the example process 500 may generate an alarm and halt further delivery of the medication fluid before the medication delivery interval expires.

Figure 6:
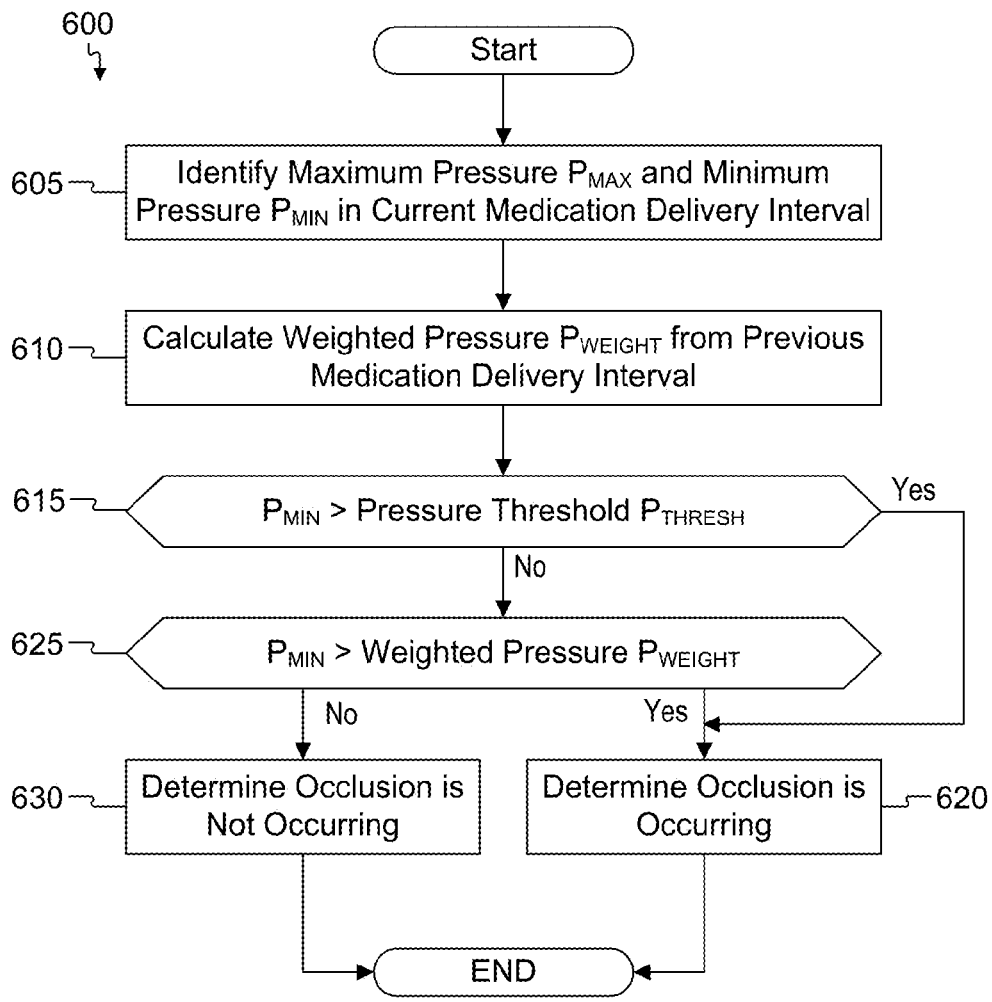
FIG. 6 illustrates a flowchart of an example method of determining that an occlusion occurred during a medication delivery interval in connection with the example process described in FIG. 5.

FIG. 6 illustrates an example process 600 for determining if an occlusion has occurred during the medication delivery interval, as briefly described in connection with FIG. 5. Initially, the example process 600 identifies a maximum pressure $P_{MAX}$ and a minimum pressure $P_{MIN}$ from the current medication delivery interval at step 605. The maximum pressure $P_{MAX}$ occurs during the delivery phase of the medication and pressure decays in the relaxation phase until it reaches equilibrium where the minimum pressure $P_{MIN}$ for the current medication delivery interval is generally determined. That is, the maximum pressure $P_{MAX}$ generally occurs at the beginning of each medication delivery interval. However, in some situations, such as an occlusion event during a movement, the maximum pressure $P_{MAX}$ may occur at any point during a medication delivery interval. Generally, the minimum pressure $P_{MIN}$ is filtered and/or averaged over several delivery pulses to remove noise in the measurements. Moreover, as will be described further below, an occlusion may be recognized by subsequent $P_{MIN}$ measurements increasing in magnitude, indicating increasing pressure due to multiple delivery pulses failing due to the occlusion and causing fluid pressure to rise.

At step 610, the example process 600 calculates a weighted pressure $P_{WEIGHT}$ from a previous medication delivery interval. Specifically, weighted pressure $P_{WEIGHT}=W*P_{MAX}+(1-W)*P_{MIN}$ where W is a weighting factor, such as 0.25, that determines the sensitivity of the occlusion detection, $P_{MAX}$ is the maximum pressure from a previous medication delivery interval, and $P_{MIN}$ is the minimum pressure from the previous medication delivery interval. In one example, the previous medication delivery interval is two intervals before the current medication delivery interval. However, in other examples, multiple previous medication delivery intervals may be used to generate the weighted pressure $P_{WEIGHT}$ in any suitable fashion, that is, by multiple comparisons, averaging the measurements, generating a detection window that adjusts based on the magnitude of the maximum pressure, and so forth. In other examples, the sensitivity may be variably adjusted based on suitable factors to ensure accurate detection of occlusions. For example, if the minimum pressure $P_{MIN}$ is sufficiently low due to the viscosity of the liquid and the maximum pressure $P_{MAX}$ is large, the sensitivity can be increased by adjusting the weighting factor W to account for more subtle changes in the minimum pressure $P_{MIN}$. Further, it should be appreciated that the method is not limited to analyzing a set of consecutive intervals indicating a problematic flow state. That is, the method should be understood to include embodiments that can accommodate intervening intervals indicating successful flow.

After calculating the weighted pressure $P_{WEIGHT}$, the example process 600 compares the current minimum pressure to a predetermined threshold pressure $P_{THRESH}$ (e.g., 3 psi) at step 615. In the event that the minimum pressure exceeds the threshold pressure $P_{THRESH}$, the example process 600 determines that an occlusion is occurring at step 620 and exits. If the minimum pressure does not exceed the threshold pressure $P_{THRESH}$, the current minimum pressure is compared to the weighted pressure $P_{WEIGHT}$ at step 625. If the current minimum pressure exceeds the weighted pressure $P_{WEIGHT}$, the example process 600 determines that an occlusion is occurring at step 620 and the example process 600 ends. However, if the current minimum pressure does not exceed the weighted pressure $P_{WEIGHT}$, the example process 600 determines that an occlusion is not occurring at step 630 and the example process 600 ends.

In another example, another exemplary method of determining if an occlusion has occurred during the medication delivery interval, as briefly described in connection with FIG. 5, may be performed by observing large fluctuations. In such an example, the method compares the current pressure profile to a smoothed profile, such as a smoothing spline fit, and tracks measurement events that deviate significantly from the smoothed curve. Using a standard deviation of pressure measurements over a period time, flow of the medication of fluid is determined to be unsuccessful if the measured pressure exceeds two standard deviations for a suitable period of time, such as 3 minutes.

Figure 7:
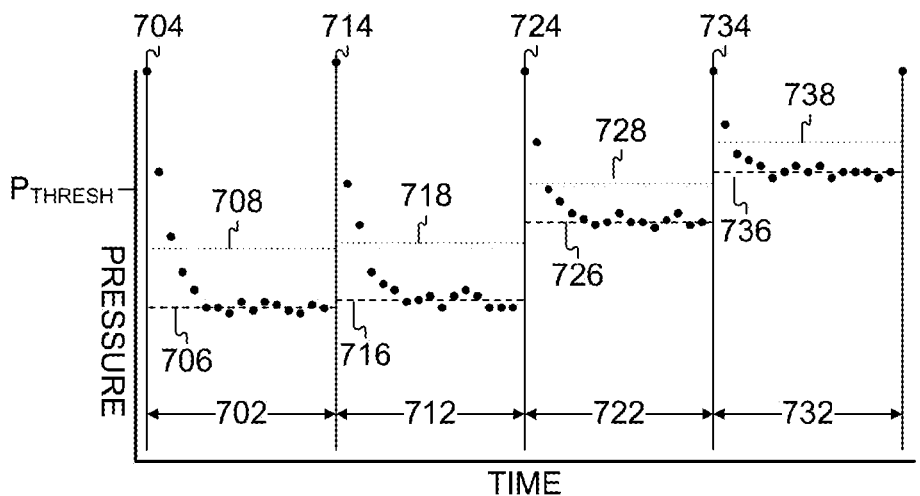
FIG. 7 illustrates an example chart of pressure measurements over four medication delivery intervals.

As noted above, the pump controller 105 compares current pressure measurements in a medication delivery interval with relevant information to determine if an occlusion is occurring. FIG. 7 illustrates a graph of example pressure measurements in an examplary medication delivery system 100 during delivery of medication to a patient and illustrates different techniques to determine if an occlusion occurs. That is, FIG. 7 is not representative of actual data and is provided to facilitate how the medication delivery system 100 can detect occlusions.

At the beginning of a medication delivery period 702, the medication delivery system 100 actuates the piston 120 to force medication in a fluid reservoir 115 to be delivered to the patient. As a result, the pressure increases in the tubing 100 and traverses toward the delivery location of the medication. In the example of FIG. 7, measurement 704 illustrates that the pressure increases at the fluid detector 125 during the initial delivery of the medication and, therefore, the maximum pressure 704 ($P_{MAX}$) occurs at the beginning of medication delivery period 702. Generally, the medication delivery system is configured to record the actual maximum pressure that occurs in the fluid path. In some examples, the medication delivery system 100 may begin recording pressure data before the expected maximum pressure occurs at the fluid detector.

As illustrated in medication delivery interval 702, the pressure decays at the fluid detector 125 after delivery of the medication in a decay region and returns to an equilibrium region where a minimum pressure $P_{MIN}$ 706 of the medication delivery period is determined. Generally, as illustrated in FIG. 7, the minimum pressure occurs in the latter portion of the medication delivery interval 702. The weighted pressure 708 can be determined using the maximum pressure 704, minimum pressure 706, and a weighting factor (e.g., 0.25) as described above.

In the second medication delivery interval 712, the maximum pressure 714 is substantially equal to the maximum pressure 704 and the minimum pressure 716 is substantially equal to the minimum pressure 706. As such, no occlusion is detected in the second medication delivery interval 712 based on the weighted pressure 708 of the first medication delivery interval because the minimum pressure 716 does not exceed the weighted pressure 708 of the first medication delivery interval 702.

In the third medication delivery interval 722, the maximum pressure 724 is substantially equal to the maximum pressure 704. However, the minimum pressure 726 increases substantially such that it exceeds the weighted pressures 708 and 718 of the previous medication delivery intervals 702 and 712. That is, the example process 600 would detect an occlusion in the third medication delivery interval 722 because the minimum pressure 726 exceeds at least one of the weighted pressures 708 and 718. As noted above, the example process 600 uses any suitable weighted pressure to detect an occlusion in the current medication delivery interval.

For the purposes of the fourth medication delivery interval 732, the effect of the detected occlusion in the third medication delivery 732 is ignored for further explanation. In fact it may be desirable for the detection method to ignore some initial number of "occlusion events" in order to eliminate noise and permit temporary occlusions to work themselves out without generating an alarm. Such a method would preferably set a minimum number of consecutive "occlusion event intervals" to be determined prior to determining that an occlusion has actually occurred. In the fourth medication delivery interval 732, the maximum pressure 734 is substantially equal to the maximum pressure 704. However, the minimum pressure 736 increases substantially such that it exceeds the pressure threshold $P_{THRESH}$. Thus, the example process 600 would detect an occlusion in the fourth medication delivery interval because the minimum pressure 736 exceeds the pressure threshold $P_{THRESH}$ without any reference to previous measurements in the prior medication delivery intervals 702, 712, and 722.

Figure 8:
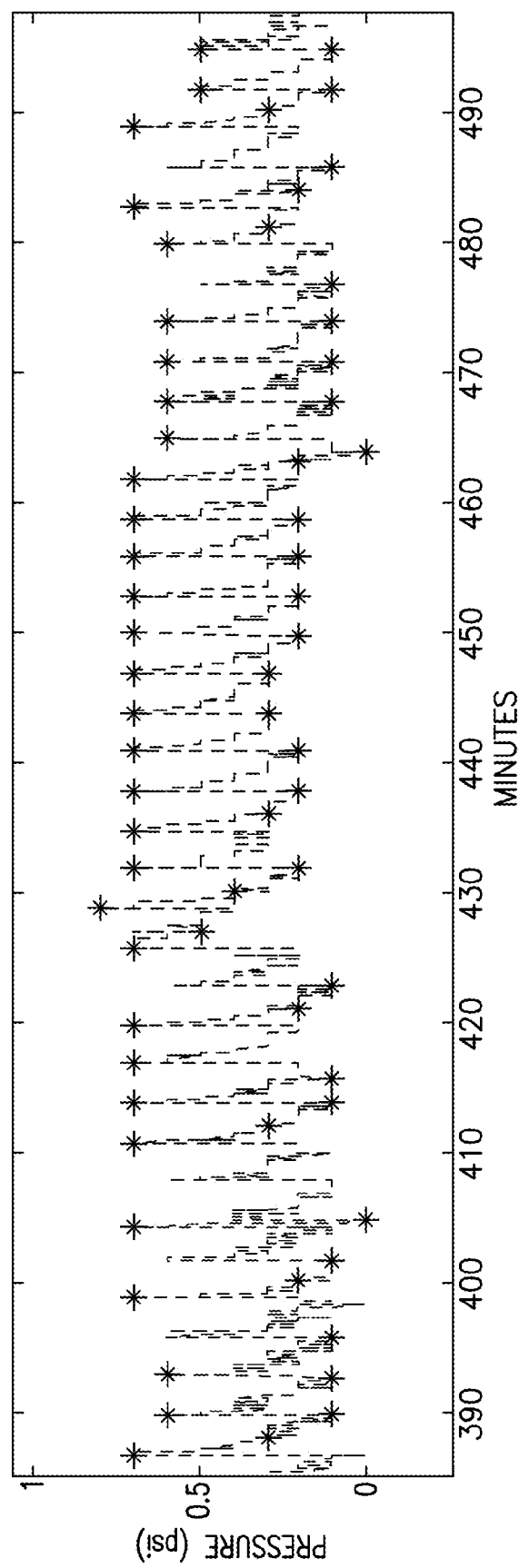
FIGS. 8 and 9 illustrate data comparing pulses to provide an indication of flow status of the fluid path using the example process described in FIG. 5.
Figure 9:
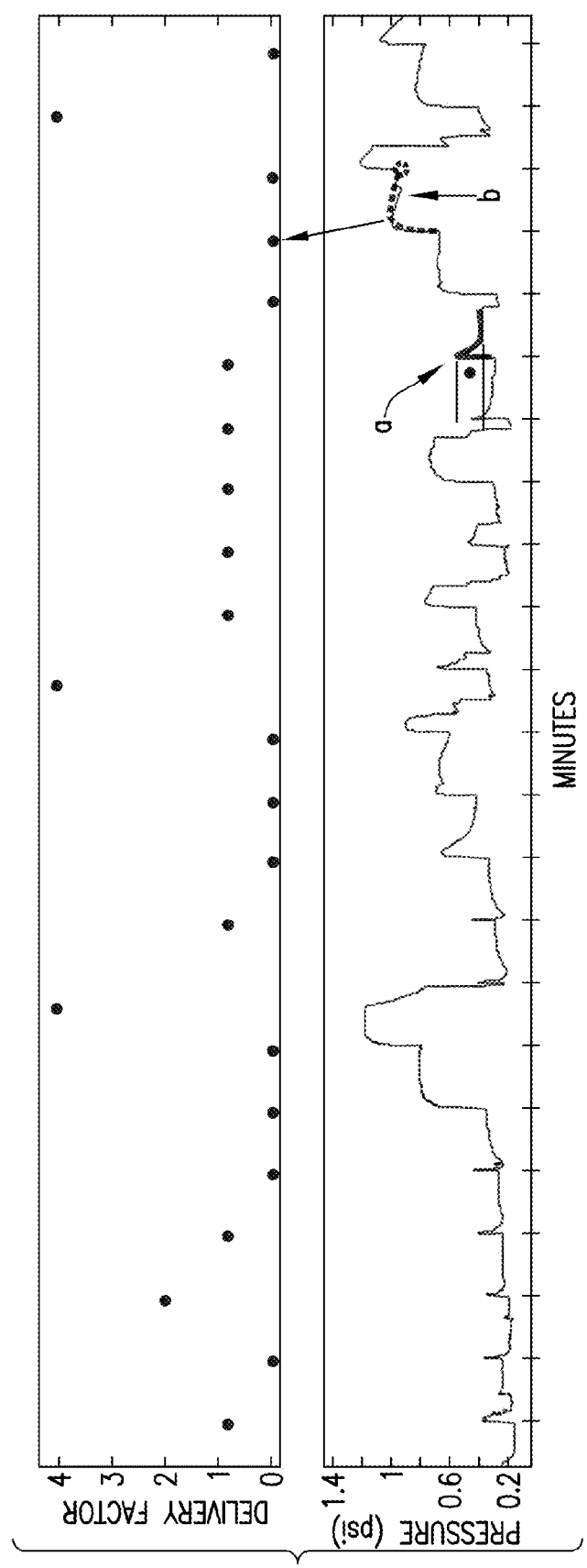

FIGS. 8-9 illustrate data from a clinical trial of an example medication delivery system 100 to evaluate efficiency of basal/bolus infusion from commercial infusion pumps. A patient was fitted with infusion sets having a sensor 310 to measure pressure to determine occlusions. Generally, pressure data was measured at a rate of 1 Hz and fixed amounts of medication were delivered in 3 minute intervals. Generally, the pressure data was analyzed by removing noise and spurious measurements, identification of minimum and maximum measure pressures, and flow was determined. For example, to capture the first peak, a second derivative of the pressure was calculated from the data illustrated in FIG. 8 and the minimum value within 160 seconds of the maximum pressure. The minimum values after the 160 second window were also recorded for further evaluation as illustrated in FIG. 8.

After determining the maximum and minimum pressures, the delivery status for each pulse (i.e., medication delivery) was determined by comparing the weighted average of the maximum and minimum pressure of the second prior pulse as described above. In the example illustrated in FIGS. 8 and 9, it was determined that comparing the immediate prior pulse did not provide a robust indication of flow status in the fluid path. Further, a threshold pressure of 3 psi was set to indicate that an occlusion has occurred in the flow path. During the clinical evaluation, in the event that an occlusion occurred, it was determined that the medical fluid was still stored in the fluid path. As illustrated in FIG. 9, a delivery factor indicates the number of medication boluses delivered in an interval. Thus, if medication fluid was flowing, the delivery factor would be 1. However, in the event and occlusion occurred, the delivery factor would be zero. Moreover, if an occlusion previously occurred and medication fluid was flowing again, the delivery factor would be greater than 1. Thus, in some examples, the medication delivery system 100 may also determine the number of medication intervals delivered to the user based on previously detected occlusions. As illustrated in FIG. 9, the medication delivery system 100 determines successful delivery of medication at point A. However, using the measured data at point B, determines that an occlusion is occurring, thereby having a delivery factor of zero. As further illustrated in FIG. 9, however, temporary occlusions may work themselves out. One such temporary occlusion is illustrated by the pressure over-time-curve s just past point B of FIG. 9. As shown, pressure increased with each pulse before, during, and after point B, but then pressure normalized, indicating that the temporary occlusion was resolved.

As described above, reliance on force data from the piston during axial movement is not necessarily correlated with flow of the medication fluid. Further, sensitivity in such a system is reduced as the fluid pressure may be masked by the dominating forces associated with static and dynamic frictional forces in the delivery mechanism, that is, the piston of the reservoir. As such, relying on force data from the piston alone detects occlusions much later or not at all compared to an in-line pressure measurement according to an embodiment of the present invention. The exemplary medication delivery system described above advantageously detects occlusions by directly measuring the pressure in the fluid path. Further, the medication delivery system is sensitive to changes in pressure over a short period of time by relying on recent pressure data to determine if suitable amounts of fluid are being delivered. Thus, the medication delivery system reduces the time to detect occlusions by using recent pressure data in conjunction with higher sensitivity to the actual fluid pressure apart from forces present in the fluid delivery mechanism.

Because the pressure is typically measured proximate to the delivery location, effects arising from compression and/or expansion of elastomeric and/or flexible elements, such as tubing, septa, and so on, are detected rapidly. That is, reliance on peak pressure $P_{MAX}$ alone may not account for changes in the fluid path. For example, a partial kink in the tubing would raise the minimum pressure and the examples described in detail above would quickly detect the partial occlusion and provide an indication if corrective action is required to maintain integrity of the medication delivery system 100.

However, measuring pressure proximate to the delivery location is beneficial for flow-based measurements. In some cases, pressure upstream from the delivery location may not be adequately detected as a result of decay in the pressure at the delivery location relative to the occlusion. Accordingly, another example may implement multiple fluid detectors 125 along or within the fluid path to detect the flow of the medication fluid at several positions in the fluid path, thereby allowing differential comparison of pressures along the fluid path to detect the location of the occlusion and facilitate medical fluid delivery. In yet other examples, a single fluid detector 125 may be implemented at any point along the fluid path.

Further, reliance on only peak pressure may not detect occlusions in the event that the minimum pressure is low. However, the medication delivery system described herein is sensitive to both low pressure and high pressure by eliminating the impact of potential forces experienced by the piston on detection sensitivity and relying on the pressure in the fluid path.

Figure 10:
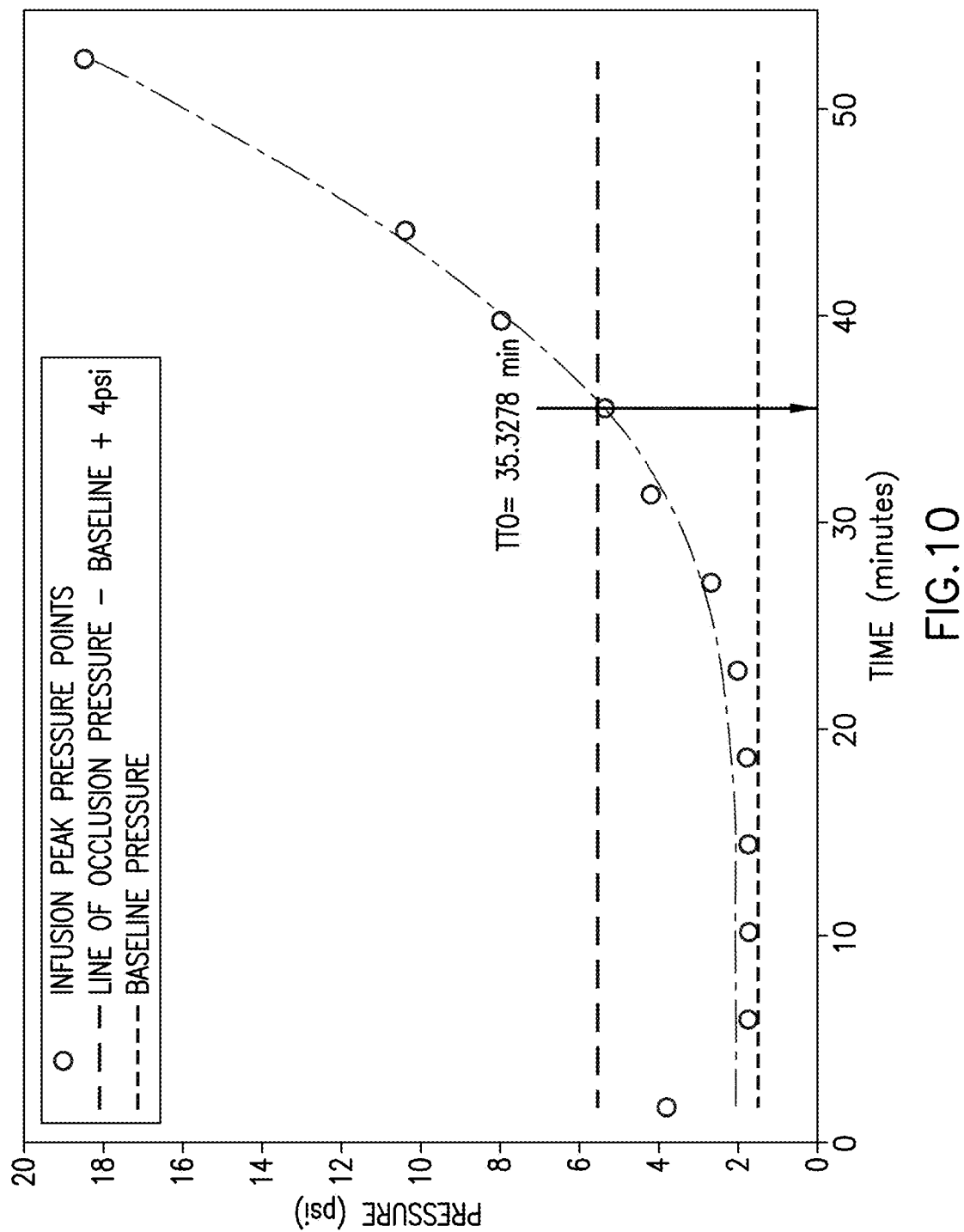
FIG. 10 illustrates data comparing peak pressure data within the peripheral IV catheter recorded during an IV infusion according to an exemplary embodiment of the invention.

In other examples, the fluid detector 125 may be implemented in continuous or temporary delivery of a medication fluid or fluid sampling or withdrawal from a patient's body via any therapeutic device, such as IV delivery of a medication fluid, a syringe, a catheter set, an infusion set hub, a pen needle, or the like. FIG. 10 illustrates peak pressure of fluid pulses flowing through an IV catheter over time. Thrombus formations that formed in the IV catheter impeded fluid flow as time increases, which consequently increased the peak pressure. Thus, in the example of an IV catheter, the fluid detector 125 could detect an occlusion to prevent potentially dangerous consequences for the patient.

Figure 11:
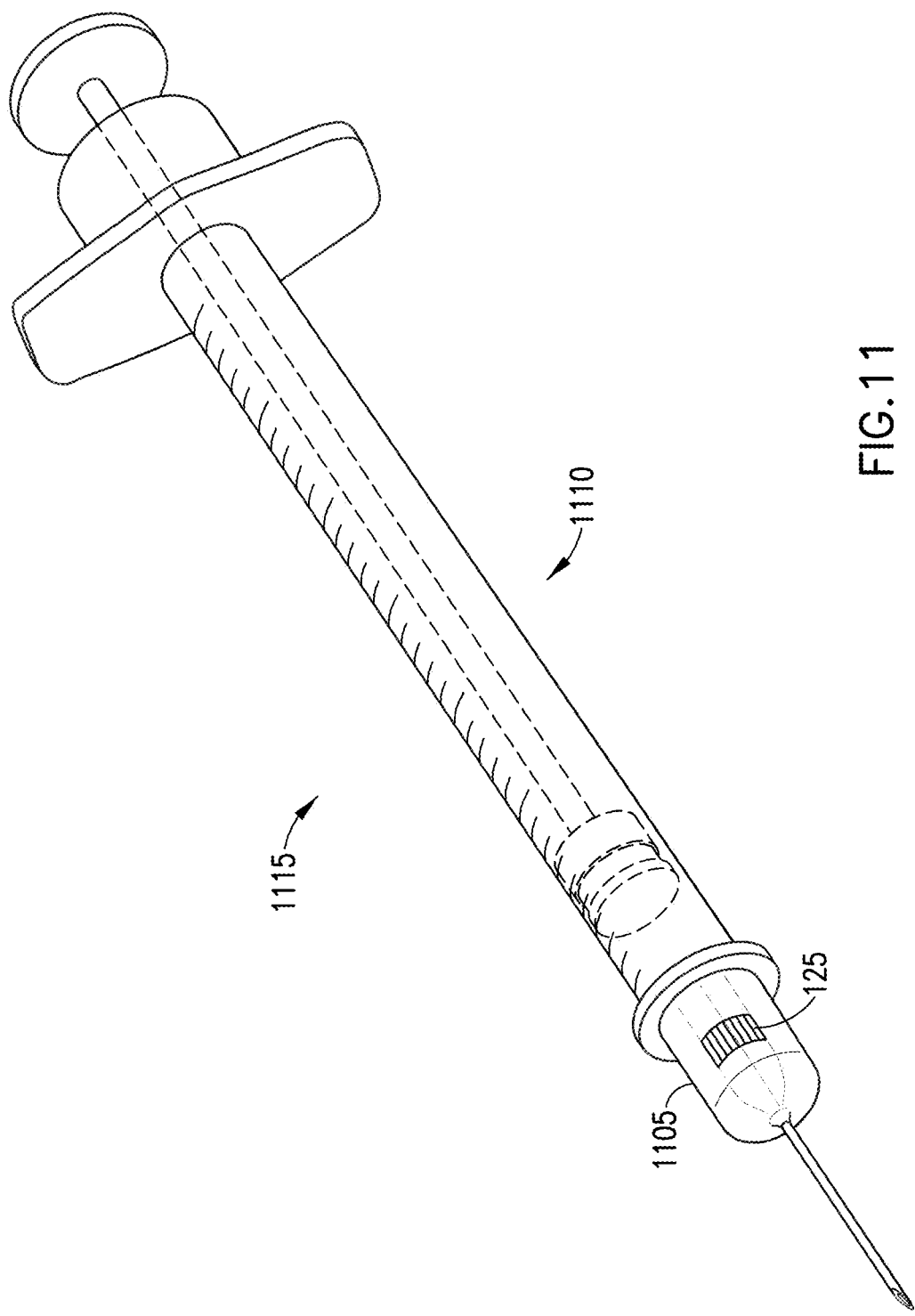
FIG. 11 depicts another example fluid detector in a needle hub of a syringe used in the medication delivery system of FIG. 1.

FIG. 11 illustrates a molded needle hub 1105 that is fastened to a needle barrel 1110 to form a syringe 1115 and is configured to communication with a fluid feedback device. The molded needle hub 1105 includes a fluid detector 125 integral therein to detect any suitable fluid characteristic such as pressure, force, and so forth. In such an example, the fluid detector 125 includes a sensor for sensing the fluid characteristic and further devices to enable to communication with the fluid feedback device, which displays the fluid characteristic.

The fluid feedback device is configured to receive information from the fluid detector 125, process the information to determine if a flow deviation is occurring that could affect the treatment of the patient and provide an indication if a flow deviation is occurring. In other examples, the fluid feedback device may be configured to stop the medical fluid communication, such as an IV delivery system for example. In the event that the fluid feedback device determines that there is a flow deviation that may affect the patient, the fluid feedback device provides an alarm to indicate that the flow deviation exists. In the example of FIG. 11, the fluid feedback device may be implemented via a touch-sensitive tablet computer that executes an application to display the processed feedback information, however any suitable device could be used, including a tablet computer, a personal computer, a proprietary device for displaying the received information, or the like.

Figure 12:
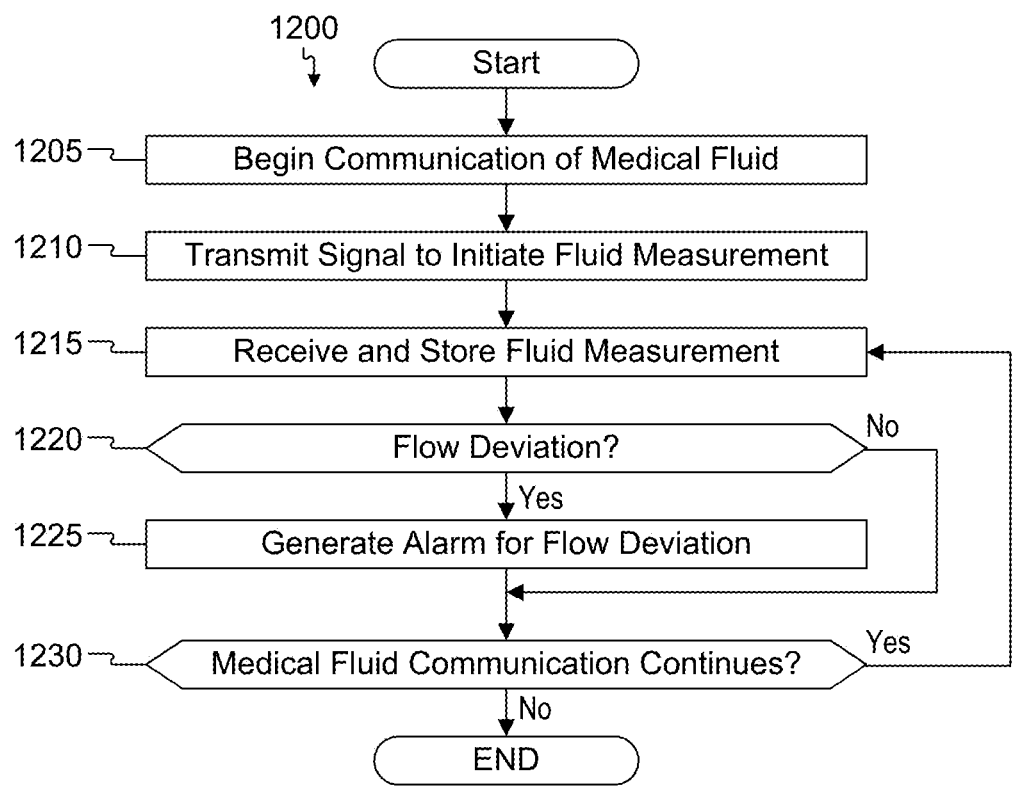
FIG. 12 illustrates another flowchart of an example process that the medication system may implement in accordance with an exemplary embodiment of the present invention.

FIG. 12 illustrates an example process 1200 to detect a flow deviation in any suitable medical fluid communication system. Initially, the example process 1200 begins with the communication of a medical fluid, such as blood, urine, antibiotics, glucose, electrolytic solutions, and so on, at step 1205. At step 1210, the fluid feedback device transmits an instruction to the fluid detector 125 to begin measuring the fluid and begins receiving measurements from the fluid detector at step 1215.

Using the receiving measurements, the example process 1200 determines if a flow deviation is occurring at step 1220. For example, the example process 1200 may implement the process 600 discussed in connection with FIG. 6 to detect a flow deviation. In other examples, the flow deviation at step 1220 could be determined by comparing the received measurement to a static or dynamic threshold. In other examples, a weighted average may be computed using a decaying average and compared to a threshold or a first and/or second derivative of the previous data and compared to a threshold. In the event that a flow deviation is detected at step 1220, the example process 1200 generates an alarm to indicate that a flow deviation is occurring at step 1225. In other examples, the medical fluid communication may be discontinued at step 1225. After generating the alarm at step 1225 or if the no flow deviation is detected at step 1220, the example process 1200 determines if medication delivery continues at step 1230. If the medical fluid communication continues, the example process returns to step 1215 to continue measuring and monitoring the flow of the medication fluid. If the medication delivery has ended at step 1230, the example process ends.

As described above, timed or scheduled replacement of PIVC catheters may be removed prematurely, thereby increasing the cost of medical treatment. The examples described above allow the medical fluid communication system to detect and provide an indication that a flow deviation occurs and, as such, the PIVC catheter should be replaced to ensure proper communication of medical fluids with the patient.

In other examples, a temperature sensor and a pressure sensor may be used in conjunction because temperature and pressure are correlated. Generally, it may be beneficial to measure the temperature in the fluid path in the event that the temperature of the medication fluctuates, thereby allowing temperature compensation to facilitate the detection of occlusions. Further, a force sensor may be implemented outside the fluid path such as, for example, a drive mechanism that connects a servo motor to the piston. In other examples, a fluid volume sensor may be implemented to detect the volume of fluid passing in the fluid path.

While the invention has been shown and described with reference to certain embodiments thereof, it will be understood by those skilled in the art that various changes in form and details may be made therein without departing from the spirit and scope of the invention as defined by the appended claims.

What is claimed is:

1. A method of detecting occlusions in a medical fluid communication system comprising a fluid reservoir, a fluid path connected between the fluid reservoir and a patient, a fluid delivery device, and a pressure sensor having a sensing surface within the fluid path in contact with the medical fluid for directly measuring a pressure of the fluid within the fluid path, the method comprising the steps of:
   measuring pressure of a medication fluid in a fluid path of a medical fluid communication system during a current interval with the in-line pressure sensor directly sensing pressure of the medication fluid;
   based on the pressure measurements, determining if a flow of the medication fluid is successful or unsuccessful;
   wherein determining if the medication fluid is flowing further comprises:
   calculating a minimum pressure of the current interval; and
   comparing the minimum pressure of the current interval to pressure data of a previous interval,
   wherein the flow of the medication fluid is not successful if the minimum pressure exceeds the pressure data of the previous interval;
   wherein the pressure data of the previous interval is based on a calculation of a peak pressure of the previous interval and a minimum pressure of the previous interval; and
   wherein the calculation is $W*P_{MAX}+(1-W)*P_{MIN}$, where $P_{MAX}$ is the maximum pressure of the previous interval, $P_{MIN}$ is the minimum pressure of the previous interval, and W is a weighting factor set based on the sensitivity.

2. The method of claim 1, wherein determining if a flow of the medication fluid is successful or unsuccessful further comprises:
   calculating a minimum pressure of the current interval; and
   comparing a minimum pressure of the current interval to a predetermined threshold pressure,
   wherein the flow of the medication fluid is not successful if the minimum pressure exceeds the predetermined threshold.

3. The method of claim 1, wherein the previous interval is two or more intervals before the current interval.

4. The method of claim 1, wherein measuring pressure of a medication fluid comprises detecting the pressure applied to a pressure sensor in a fluid path connected between the fluid reservoir and a patient.

5. The method of claim 4, further comprising:
   if the flow of the medication fluid is unsuccessful, determining if the flow of the medication fluid in the fluid path can be resolved; and
   attempting to correct the flow of the medication fluid.

6. The method of claim 4, further comprising, if the flow of the medication fluid is unsuccessful, generating an alarm indicating an occlusion has occurred.

7. The method of claim 6, further comprising halting further medication fluid from flowing into a patient until the flow of the medication fluid is resolved by a user.

8. A method of detecting occlusions in a medical fluid communication system comprising a fluid reservoir, a fluid path connected between the fluid reservoir and a patient, a fluid delivery device, and a pressure sensor having a sensing surface within the fluid path in contact with the medical fluid for directly measuring a pressure of the fluid within the fluid path, the method comprising the steps of:
- measuring pressure of a medication fluid in a fluid path of a medication fluid communication system during a current with the pressure sensor directly sensing pressure of the medication fluid;
- comparing the minimum pressure of the current interval to a predetermined threshold pressure, wherein the predetermined threshold is based on a calculation of a peak pressure of the previous interval and a minimum pressure of the previous interval wherein the calculation is $W*P_{MAX}+(1-W)*P_{MIN}$, where $P_{MAX}$ is the maximum pressure of the previous interval, $P_{MIN}$ is the minimum pressure of the previous interval, and W is a weighting factor set based on the sensitivity; and
- determining if a flow of the medication fluid is not successful if the minimum pressure exceeds the predetermined threshold and determining if the flow of the medication fluid is successful if the minimum pressure does not exceed the predetermined threshold.

\* \* \* \* \*